United States Patent [19]

Benney et al.

[11] 4,175,037
[45] Nov. 20, 1979

[54] PROCESS FOR PACKING CHROMATOGRAPHIC COLUMNS

[75] Inventors: Charles H. Benney, Stamford, Conn.; Thomas J. Filipi, Landenberg, Pa.

[73] Assignee: Whatman Inc., Clifton, N.J.

[21] Appl. No.: 894,716

[22] Filed: Apr. 10, 1978

[51] Int. Cl.[2] .............................................. B01D 15/08
[52] U.S. Cl. ...................... 210/31 C; 55/67; 210/DIG. 22
[58] Field of Search ............ 55/15, 67, 197, 386, 55/277; 73/23.1, 61.1 C, 422 GC; 210/31 C, 148 C

[56] References Cited

U.S. PATENT DOCUMENTS

| | | | |
|---|---|---|---|
| 2,845,136 | 7/1958 | Robinson | 55/386 |
| 3,164,980 | 1/1965 | Lord | 55/67 X |
| 3,248,856 | 5/1966 | Guillemin et al. | 55/67 |
| 3,429,743 | 2/1969 | Branson | 55/15 |
| 3,522,172 | 7/1970 | Pretorius et al. | 55/67 X |
| 3,692,669 | 9/1972 | Bauman | 210/31 C |
| 3,796,657 | 3/1974 | Pretorius et al. | 210/31 C |

Primary Examiner—John Adee
Attorney, Agent, or Firm—Lerner, David, Littenberg & Samuel

[57] ABSTRACT

Methods for packing chromatographic columns are disclosed, including introducing a packing material into a chromatographic column under the influence of a first pressure differential until the column is filled to a desired extent with the packing material, and subsequently establishing a substantially regular periodic vibration along the length of the column and subjecting the packing material to a second pressure differential, which is preferably greater than the first pressure differential. The substantially regular periodic vibration can comprise ultrasonic vibration, which is preferably applied to the column by immersing it in a liquid bath and subjecting the liquid bath to ultrasonic vibrations.

33 Claims, 2 Drawing Figures

PROCESS FOR PACKING CHROMATOGRAPHIC COLUMNS

FIELD OF THE INVENTION

The present invention relates to chromatography. More particularly, the present invention relates to methods for packing chromatographic columns with a particulate packing material.

BACKGROUND OF THE INVENTION

Chromatography, in all its forms, is a technique used to separate a mixture of compounds or elements into its individual components. All chromatographic processes consist of two basic segments: a mobile phase and an immobile phase. The mobile phase moves through a capillary or tube, called a column, containing the immobile phase, and the sample to be separated into its basic components is injected into the mobile phase moving through the column. As the sample is swept forward by the mobile phase, the sample components are either adsorbed on the surface of the immobile phase (if the immobile phase is a solid) or dissolved in the immobile phase (if it is a liquid). As the mobile phase continues passing through the column, components of the sample are continuously desorbed back into that mobile phase. This adsorption-desorption process continues throughout the length of the column, each sample component in the mobile phase thus moving through the column at a different rate, depending primarily upon its attraction for the immobile phase. The components therefore separate as they pass through the column and emerge at the other end of the column at different times.

In liquid chromatography, the sample which is to be analyzed is a combination of liquid components which are carried through the column in the liquid phase by a mobile phase comprising a liquid carrier stream. The immobile phase in liquid chromatography generally comprises a solid in the form of uniform or other particles packed in the column.

In gas chromatography, the sample to be analyzed comprises volatile components which are carried through the column in a gaseous state by an inert mobile phase in this case, called the carrier gas. The immobile phase is either a solid in the form of uniform or other particles, or a thin film on either the particles and/or the column walls.

Therefore, under proper gas chromatographic conditions, various components of the gas sample are spacially separated by the above-described process of selective adsorption and desorption, so that the separated gas constituents issue from the end of the column in sequential order corresponding to their relative volatility, their molecular weight or some other property affecting the degree of adsorption on the immobile phase or packing material in the column. As these separated gases emerge from the column they are normally passed through a suitable detector element which measures a property of the gas indicative of the character and/or amount present.

The immobile phase or packing most commonly used in chromatographic columns includes diatomaceous earth, alumina, glass beads, fluoro carbons, silica gel, and the like. Conventionally, the packing in whatever form is chosen for a particular chromatographic column, is poured into the column in granular form and compacted therein by vibration, tamping or the like. To operate these gas chromatographic columns an inert gas such as helium, argon or nitrogen acts as the carrier gas for the sample, and flows continuously through the column. The use of such an inert mobile carrier gas insures that the carrier gas does not react with either the sample or the immobile phase. The samples are introduced into the carrier gas either as a liquid or a gas. Usually, liquid samples generally on the order of ten microliters or less, are injected rapidly into a chamber which is maintained at a temperature that insures quick and complete vaporization of the sample.

The efficiency of these columns determines the length of time it takes in order to perform a given analysis. That is, columns having high efficiencies can be of shorter length than columns having low efficiencies, and with the carrier gas flowing at the same rate the analysis can be performed much more readily. It is therefore desirable to improve the efficiency of a column for two principal reasons, i.e. that a column of high efficiency can perform an analysis much more rapidly, and that a column with high efficiency will have a greater ability to separate two sample components (or to resolve them) and hence the capability of analyzing products more precisely than will a column of standard efficiency having an equivalent length.

The efficiency of chromatographic columns is generally expressed in terms of theoretical plates, which is simply a number of theoretical plates per unit of length necessary to effect resolution. As a component in a sample is moved through the column by a carrier gas, the velocity at which the component is traveling, the dimensions of the column, the medium through which it travels and the packing density will have a direct influence on the column efficiency. As the packing density increases, however, there is a commensurate and undesirable pressure drop increase across the packed portion of the column.

Many techniques have heretofore been developed for packing chromatographic columns. Thus, for example, U.S. Pat. Nos. 2,845,136 and 3,164,980 each describe packing techniques wherein the packing material is poured into the chromatographic column and compacted therein by vibration, tamping or the like. Also, U.S. Pat. Nos. 3,248,856; 3,522,172; 3,692,669 and 3,796,657 disclose packing techniques wherein the packing medium is fluidized by various techniques and then allowed to settle to form a packed bed. In "GAS CHROMATOGRAPHY 1960" edited by R. P. W. Scott, published by Butterworths (London) at pages 240 et seq., the effect on packing structure of various modes of vibration, tapping, rotations or combinations thereof is disclosed.

"A STUDY OF PACKED CAPILLARY COLUMNS," by V. G. Berezkin et al, Journal of Chromatography, 99 (1974) pgs. 111–122, discloses the packing of columns by simply tapping the packed column lightly by hand or by moving a mechanical vibrator along the column. The authors also disclose the filling and packing of such columns utilizing a combination of an inert gas flow and low-frequency (50–100 Hz) electromechanical vibrators located at several positions along the column.

In "PERMEABILITY AND PREPARATION OF MICRO-PACKED COLUMNS," by J. A. Rijks et al, Chromatographia, Volumn 8, No. 9 September 1975, pages 482 et seq., the authors disclose simultaneously filling and packing a micropacked column (i.e. having a particle/column diameter rate between 0.1 and 0.3)

with the use of gradually increasing pressure and ultrasonic vibrations. The authors also disclose that a hand vibrator held on the surface of the container is employed to assist in providing a continuous stream of particles to the column.

Finally, In "POTENTIALITIES OF MICROPACKED COLUMNS SOME APPLICATIONS IN PETROLEUM CHEMISTRY," C. A. Cramers, J. Rijks and P. Bocek, J. Chromatography, 65 (1972) 2937, a continuation of ultrasonic vibration and pressure is employed to simultaneously fill and pack a chromatographic column. This article also notes that at the start of the procedure the pressure increase shall be very gradual, and continues that care should be taken to maintain a substantially constant pressure product across the packing to ensure a homogeneous packing density.

Despite the many techniques currently available, all of which employ various combinations of pressure and vibration, those skilled in the art still recognize the need for a packing technique which will maximize packing density while still imposing a relatively low pressure drop across the packed portion of the column.

Accordingly, it is an object of the present invention to provide a packing technique which enables high separation efficiencies to be obtained.

It is another object of the present invention to provide a packing method which enables maximum packing densities to be obtained while still maintaining a relatively low pressure drop across the column.

It is a still further object of the present invention to provide a packing method which is capable of increasing separation efficiency of chromatographic columns.

SUMMARY OF THE INVENTION

In accordance with the present invention, the applicants have discovered that these and other objects can be accomplished by packing a chromatographic column by introducing a packing material into the chromatographic column under the influence of a first pressure differential until the column is filled to a desired extent with the packing material, and subsequently establishing a substantially regular periodic vibration along the length of the column and subjecting the packing material to a second pressure differential.

In a preferred embodiment of the present invention, the second pressure differential is greater than the first pressure differential, and preferably the substantially regular periodic vibrations along the length of the column comprise ultrasonic vibrations, preferably produced by immersing the column in a bath of liquid and subjecting that liquid bath to ultrasonic vibrations.

In another embodiment of the present invention, the first and second pressure differentials are maintained by introducing a fluid such as an inert gas stream into the column, and preferably also by applying a vacuum to the end of the column.

In another embodiment of the present invention any static charge on the packing material is reduced; for example where an inert gas stream is utilized, the gas stream may be pressed into contact with a radiation source prior to its entry into the column, or in another embodiment, the particles in the column are heated for that purpose.

In a preferred embodiment of the present invention where an inert gas stream is used to produce the first pressure differential the column is purged of inert gas prior to establishing the substantially regular periodic vibrations along the lengths of the column thereafter. Most preferably the column is subjected to the second pressure differential immediately after the establishment of the substantially regular periodic vibration along the length of the column, preferably comprising ultrasonic vibrations.

In another embodiment of the present invention, the second pressure differential is established substantially instantaneously, and in another embodiment irregular vibrations are applied to the column during the introduction of the packing material under the influence of the first pressure differential. These irregular vibrations can preferably be produced by tapping on the column itself.

In another embodiment of the present invention, a plurality of steps are employed in connection with the introduction of the packing material into the column under the influence of the first pressure differential, with a portion of the packing material being introduced into the column in each of those steps. Preferably, irregular vibrations are applied to the column during each of those steps.

BRIEF DESCRIPTION OF THE FIGURES

The present invention will be further understood by reference to the attached drawings wherein.

DETAILED DESCRIPTION

The method of the present invention can be applied to a variety of chromatographic columns employing a variety of packing material therein. The columns can include glass and metallic columns, and can include columns generally referred to as microbore columns (i.e. generally having an inside diameter of between about 0.7 and 1.2 millimeters), and macrobore columns (i.e. those having inside diameters greater than about 1.2 millimeters.) This technique can also be applied to such columns used for both liquid and gas chromatographic purposes. While a variety of packing materials can be utilized in connection with the method hereof, it must be borne in mind that certain types of packing materials will not be susceptible to the technique of the present method. That is, they cannot be packed more efficiently in accordance with the present invention in order to achieve the improved results which can be utilized therewith. It is thus necessary that the packing material utilized have a sufficiently low friability or high crush strength during packing so as to avoid crushing or disintegration during packing under the conditions employed herein. If the materials utilized thus cannot maintain a substantial degree of their physical characteristics during packing, including the application of vibrations and pressures in accordance with this method, then the improved results achievable in accordance herewith cannot be realized with such packing materials.

Bearing this in mind, the packing materials which can be employed in connection with the present invention include a number of conventional chromatographic packing materials, generally comprising inert solids such as diatomaceous earth, alumina, glass beads, teflon beads, graphitized carbon black, molecular sieves, silica gel (generally used in conjunction with high-pressure liquid chromatography) and the like. These inert packings of support materials are preferably of uniform particle size and will generally range from about 5 to about 200 microns in particle size.

Figure 1:
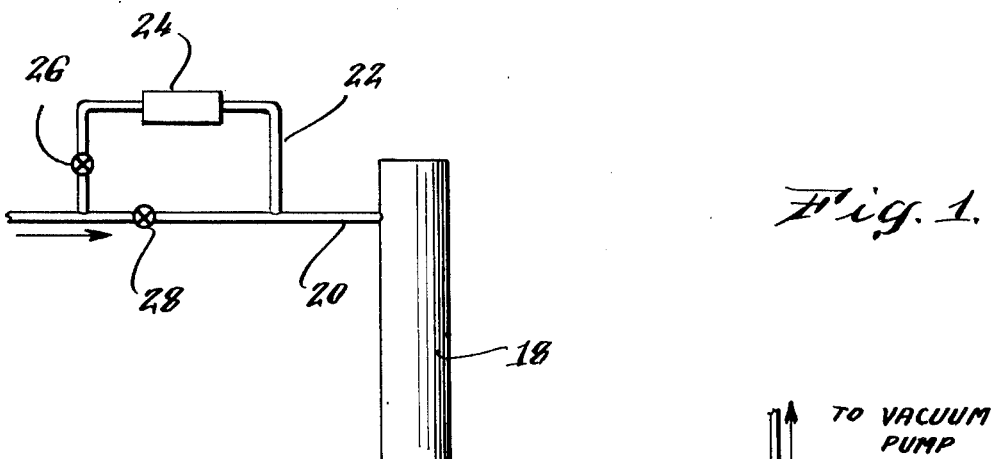
FIG. 1 is a schematic diagram illustrating an apparatus in which the method for packing a chromatographic column in accordance with the present invention can be effected.
Figure 1:
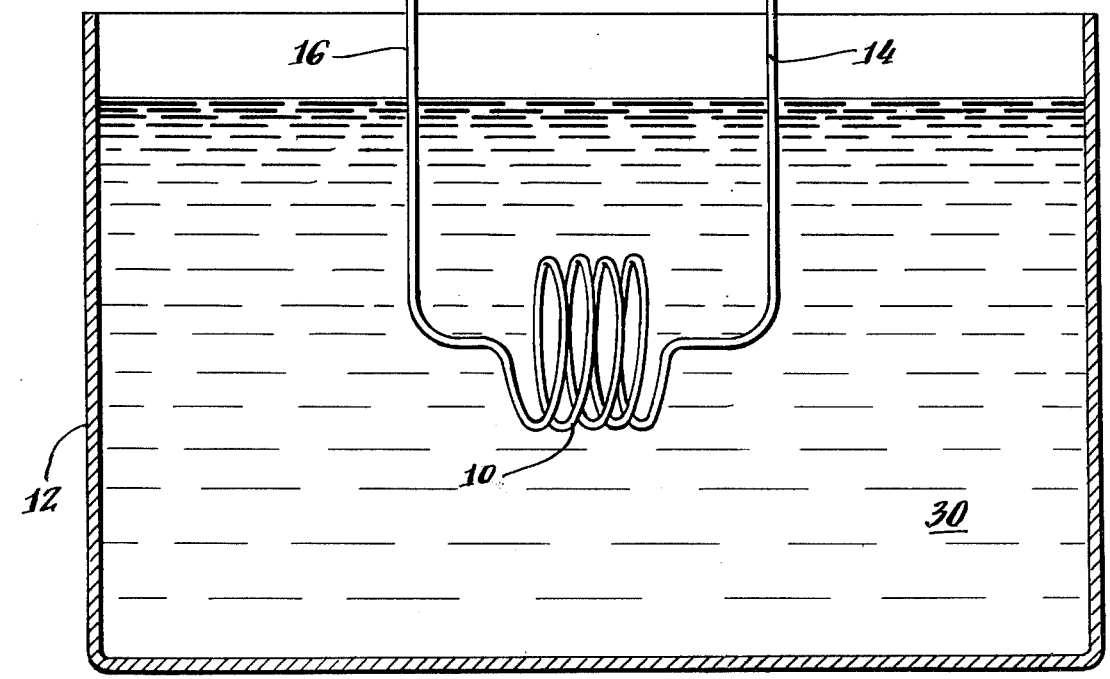

Referring to the Figures, in which like numerals refer to like portions thereof, FIG. 1 shows an apparatus for packing a conventional chromatographic column such as a conventional glass spiral column 10 which is immersed in a water bath 12. The water bath can be made to cavitate by imparting ultrasonic vibrations thereto in a conventional manner. The effluent line 14 from the column leads to a vacuum pump (not shown), while the inlet line 16 to the column is connected to a reservoir 18 which contains the column packing material. The reservoir 18, in turn, is connected to an inert gas feed line 20. Of course, where a liquid is to be utilized instead of the inert gas, such as for packing a column for use in high pressure liquid chromatography, analogous apparatus for applying such a liquid will be employed. In instances wherein the packing material has been deactivated, e.g. wherein the particles are treated with a silanizing reagent, the inert gas can be fed to the reservoir 18 through a line 22 whereby the inert gas is exposed to a radioactive source 24 which expels ions into the gas stream for static elimination purposes. The inert gas can be fed directly into the reservoir 18 via line 20 by closing valve 26 and opening valve 28. Conversely, when it is desired to pass the inert gas through the radioactive source 24 and into the reservoir via line 22, valve 26 can be opened and valve 28 shut.

Before commencing the packing procedure of the present invention, it is generally necessary to first prepare the packing material therefor. Thus, for example, for most gas-liquid chromatography applications, it is generally considered preferable to pretreat the inert support materials to impart a silane coating thereto. This is conventionally effected by reacting surface silanol groups with organic silane compositions, e.g. dimethyldichlorosilane. In any event however, the particles are first pretreated to remove generally inorganic surface impurities from the support material by washing that material with acid. Preferably the material is then treated to neutralize the acid and then dried.

In the case of gas chromatography, the inert support materials can then be coated with a stationary liquid phase. Nearly any unreactive non-volatile liquid can be used as the stationary phase. As a general rule, the boiling or decomposition point of this liquid should be substantially above the column operating temperature in order to minimize its gradual vaporization. These stationary liquids can be divided into two groups: that is, those used in separations based upon non-selective columns, i.e. where the separations are mainly due to differences in vapor pressures or diffusion rates of the components, and these liquids include silicon oils, greases and the like, and those used in separations based upon selective columns where there is a preferred interaction of components with the stationary liquid phase based upon complementary chemical structures, and these liquids include esters, alcohls, acids, amines and the like. Typical stationary liquid phases include mineral oil, di-octyl phthalate, di-nonyl phthalate, silicone, methyl silicone, nitrobenzene, tricresyl phosphate, dibutyl phthalate and the like. Particularly where the support material is porous in nature, it is preferable to degas the system after pouring the liquid over the support in order to assist the liquid in entering the pores of this support material. Once the support or packing materials are coated with the stationary phase, they can then be filtered and dried, preferably with nitrogen, in order to remove any solvent therefrom. The support can then be loaded into reservoir 18, and the packing procedure is ready to commence.

A chromatographically and chemically inert porous retainer is inserted into the terminal portion of the column proximate the junction of the column passageway with the outlet 14, in order to prevent loss of the packing material. Such retainers can be formed of fiber glass, glass wool, glass frits, an inert metal fiber or wool such as gold wool and the like. Such retainers can eventually be interposed in the terminal portions of the inlet and outlet lines leading to and from the column to further protect against loss of packing material. The chromatographic column 10 is attached to the inlet 16 from the reservoir 18 and the outlet 14 leading to the vacuum pump and is then immersed in the water 30 contained within the ultrasonic bath 12. The packing apparatus is preferably kept in a room in which humidity can be controlled so that packing is effected under dry conditions.

The packing process includes an initial "soft" packing of the inert support or packing material into the column under a mild pressure differential. Preferably, the column is first flushed with a stream of dry inert gas such as dry nitrogen, argon and the like. The packing operation is then initiated with the periodic addition of the packing material under the influence of a first pressure differential through the column. This pressure differential can be established either by using an inert gas pressure as discussed above, or preferably by means of a vacuum applied to the column, or most preferably by utilizing both such an inert gas pressure and a vacuum. This is conducted in a manner so as to feed the packing material into the column so as not to result in a segregation of the particles in terms of various particle sizes therein. Preferably, while maintaining the first pressure differential across the column separate portions of the packing materials are added to the column, and irregular vibrations can be applied to the column, such as by periodically tapping or rapping reservoir 18, or as an alternative cavitating the ultrasonic bath for short periods, for example up to about 2 seconds, to achieve similar effects. Such procedure is carried out in order to remove any blockage which may be present in the column. At the same time, the presence of substantially regular periodic vibration along the length of the column is avoided during this stage of the packing process, such as by cavitating the ultrasonic bath for significant periods of time throughout the packing operation. In other words, what must be avoided is the establishment of a regular wave form within the column, e.g. sinusoidal, triangular, square, etc., so that random loading of the column is insured without the segregation of particle sizes mentioned above.

As for the actual pressure differential which is established during this soft packing phase of the method of the present invention, this will depend somewhat on the type of column and the type of packing being applied therein. Thus, the linear gas velocity achieved by any given flow of fluid or gas through the column will be dependent upon the size of the column bore and the average particle size of the packing material so utilized. As a specific example (for gas chromatography), with a microbore column having a diameter of between about 0.7 and 1.2 millimeters, and utilizing particles having an average particle size of between about 5 and 75 microns, preferably between about 37 and 44 microns, a first pressure differential high enough to initiate movement of the particles from the reservoir into the column, such as between about 5 and 50 pounds per square inch differential (psid.) per yard of column length will generally be employed. On the other hand, with a macrobore column having a diameter of above about 1.2 millimeters and utilizing a packing material having an average particle size of between about 50 and 200 microns, preferably between about 74 and 84 microns, a first pressure differential between about 5 and 25 psid per yard of column length will be utilized.

Once the column is filled with the packing material to the extent desired, the pressure differential employed in filling the column is substantially abated, for example where the fluid is a gas, the vacuum is continued at the column outlet for a short period, e.g. 15 minutes. At this point cavitation of the ultrasonic bath can be commenced. The bath will generally cavitate when exposed to an ultrasonic frequency above about 15 kilohertz. Once ultrasonic vibration is commenced along the length of the column the packing material can then be subjected to a second pressure differential, greater than the first pressure differential utilized and again dependent upon the size of the column bore and the average particle size of the packing material utilized. Once again, increased particle size packing material will generally permit the use of lower pressure differentials therein. Utilizing a flow of inert gas to establish the second pressure differential, the differential is substantially instantaneously produced in the column so as to jolt the packing material previously soft packed in the now vibrating column.

While the use of ultrasonic vibration has been discussed above, the significant factor is that in this second phase a substantially regular periodic vibration is established along the length of the column. While the use of fairly short wave length vibrations such as those comprising a low multiple of the average particle diameter of the packing materials are preferred, it is possible to employ longer wave lengths. It is therefore possible to use sonic vibration therein preferably with higher energies therewith. The significant fact is that there is a substantially constant vibration produced in the bed and the packing particles act like a fluidized bed therein. Preferable frequencies of between about 30 and 60 kilohertz are employed. This procedure results in a maximization of packing density within the column and the concomitant significant improvements realizable in accordance with the present invention. This second phase can preferably be continued for a period of between about 5 minutes up to about 10 hours, although generally periods of between about 5 minutes and 30 minutes are sufficient. Again considering the previous discussion with respect to the relationship between the pressure differential utilized and the inside diameter of the column as well as the average particle size of the packing material utilized, generally in a microbore column utilizing packing materials having average particle sizes as described above, in this step a pressure differential of between about 50 and 500 psid per yard of column length will be utilized. On the other hand, with a macrobore column utilizing packing materials having average particle sizes as described above, a pressure differential of between about 25 and 250 psid per yard of column length will be utilized. Generally the second pressure differential must be sufficient to settle the bed and obtain maximum packing density, but cannot be too great so that the gas velocity within the column is elevated to a point where the particles being utilized tend to immobilize or jam and cannot be sufficiently packed therein.

After the application of this second pressure differential and substantially regular vibration along the column the ultrasonic bath is turned off and the fluid pressure is terminated. Any residual pressure is allowed to reduce to ambient pressure slowly so as to avoid disturbing the packing in the column and any residual fluid in the system is allowed to slowly bleed off. Thereafter, the packed chromatographic column can be disconnected from lines 14 and 16 and a porous retainer as described hereinabove can be inserted into the initial portion of the continuous passageway of the column proximate the junction of the passageway with the inlet 16 thereby sealing the packing within the passageway of the column. It has been found that columns packed in this manner exhibit significantly higher separation efficiencies than have heretofore been obtainable by other known prior art techniques. Moreover, even though the packing density is maximized in accordance with the method of the present invention, it has been found that the pressure drop across the column is still relatively low. The packing technique of the present invention enables the obtaining of significantly greater column efficiencies, for example, with a typical gas chromatography microbore column, column efficiencies of up to about 1,000 plates per foot were previously achievable, but in accordance with the present invention it is possible to achieve column efficiencies of between about 2,000 and 3,000 plates per foot. On the other hand with a typical gas chromatography macrobore column it was previously possible to obtain consistent column efficiencies of between about 200 and 800 plates per foot, and in accordance with the present invention efficiencies of between about 1,000 and 1,500 plates per foot can now be achieved. Again, however, each of these specific efficiencies relate to the particular column under consideration, and will vary with the diameter of the column bore, the particles being employed, etc.

Figure 2:
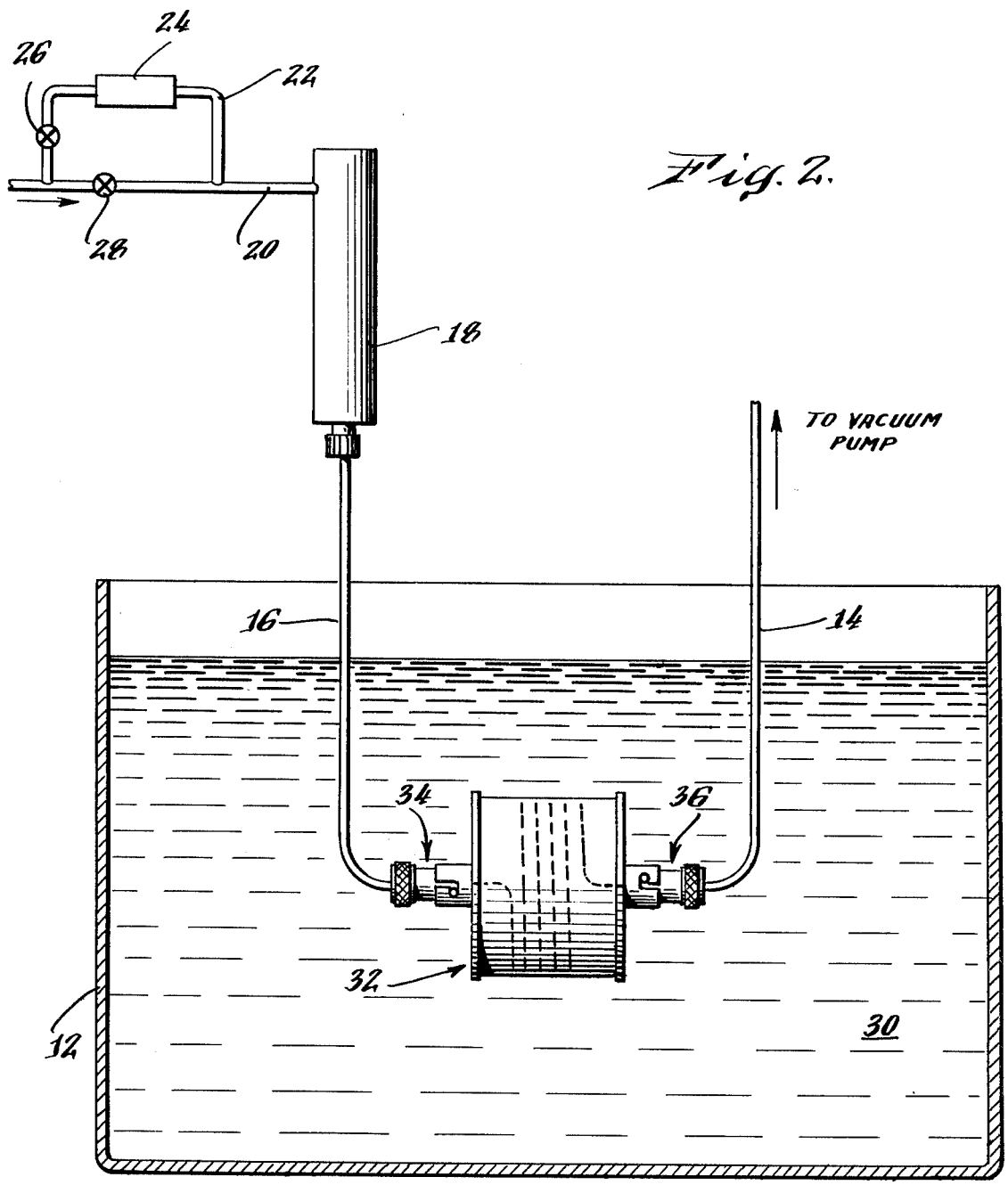
FIG. 2 is a schematic diagram illustrating an apparatus for effecting the method of the present invention used in conjunction with a monolithic glass chromatographic column.

Referring to FIG. 2, another embodiment of the present invention is shown wherein a monolithic glass chromatographic column 32 is shown being packed in accordance with the method of the present invention. The monolithic glass chromatographic column has a continuous passageway formed therethrough which can be packed with chromatographic packing material in accordance with the present invention. Quick-connect and disconnect couplings 34 and 36 enable the column to be connected and disconnected from the packing system of the present invention. Moreover, these couplings enable the packed chromatographic column to be readily connected to gas feed and analytical devices.

If it is desired to further eliminate the static charge carried by the packing particles, the use of radiation source 24 can be employed or alternatively or in combination therewith, the inside diameter of the passageway through the chromatographic column can be coated with a non-reactive and non-catalytic metal such as gold, such as by conventional vacuum metallizing techniques.

DESCRIPTION OF PREFERRED EMBODIMENT

With reference to FIG. 1 an apparatus as shown therein was utilized wherein the effluent line 14 was connected to a ballast chamber of approximately 6 gallons capacity. The ballast chamber was then connected to a Precision Scientific Corporation model D-75 vacuum pump, and a Whitey ball valve was included in effluent line 14 in order to permit rapid opening of the effluent line to the ballast chamber. The ballast chamber was used in order to provide a greater reservoir of vacumm for the system.

The column employed was a 6 foot long glass coil ¼ inch O.D. by 2 millimeters I.D. configured to fit a Hewlett-Packard 5700 gas chromatograph, column configuration 5. The reservoir 18 consisted of a 1 foot length of ⅜ inch 0.D. by 0.280 inch I.D. stainless tube connected to the inlet line 16 by means of a SWAGELOCK ⅜ inch to ¼ inch brass reducing coupling which had been drilled through to ¼ inch I.D. to permit insertion of the column into the reservoir above the level of the fitting. The top of the reservoir was fitted with a SWAGELOCK ⅜ inch single-end shut-off quick connect coupling which then connected to a Whitey ball valve 28. In this example, the inert gas was fed directly into the reservoir 18 through line 20.

The upstream or high pressure end of the Whitey ball valve 28 was connected by means of a SWAGELOCK ¼ inch single end shut-off quick connect to a supply of nitrogen with a regulator which could control between 0 and 200 psig. The ultrasonic bath 12 was a BRANSONICS model B-52 bath and the fluid in the bath was water with a small amount of bis(2-ethylhexyl)sulfosuccinate, sodium salt in order to reduce the surface tension and permit better transduction of the ultrasonic vibration. The support employed was prepared from 30 to 60 mesh CHROMOSORB G which was ground and screened to produce a support having a narrow range particle size of between about 100 and 110 microns, employing electroformed round holed screens as supplied by Stork America Corporation. The ground support was then washed exhaustively with 8 N hydrochloric acid until the supernatant had no detectable yellow coloration.

After acid washing the support was rinsed with deionized water until the supernatant was neutral and there was no detectable clouding of the supernatant due to fines. The support was dried overnight in a 110° C. oven, allowed to cool, and then coated with liquid phase. Coating was accomplished by transferring a weighed quantity of support to a round bottom ground joint flask and covering with a solution of 5% CARBOWAX 20M in ethylene dichloride (weight per volume), in the proportion of 2 milliliters of coating solution to each gram of support. The resulting slurry was then degassed by subjecting it to a vacuum while vibrating in an ultrasonic bath in order to insure complete penetration of the coating solution into the pores of the support. The slurry was transferred to a coarse frit Buchner funnel with an additional amount of coating solution (also in the proportion of 2 milliliter per gram of support) used as a rinse to effect complete transfer. The slurry was then filtered under vacuum until the solution ceased to drip freely from the end of the funnel. The damp support was then transferred to a fluidized bed drier (HI-EFF fluidizer manufactured by Applied Science Laboratories) and dried by fluidizing with a stream of warm nitrogen. Five grams of the resulting packing material was introduced to the reservoir 18, the system was reconnected and filling was commenced.

With the valve 28 closed and with the valve between the effluent line 14 and the ballast tank also closed, the ballast tank was evacuated. The valve in the effluent line was then opened and the reservoir 18 tapped periodically to assist the flow of the packing material into the column. When the filling process slowed, with 0 psig. on the nitrogen regulator, valve 28 was opened to continue the filling process. When the filling process again slowed, valve 28 was closed, 20 psig. was applied from the nitrogen regulator, and valve 28 was again opened to complete the filling process. With the column full and no visible voids therein, a timer was then set for 15 minutes during which time the vacuum pump was allowed to continue to evacuate gas from the column. At the end of this time period the nitrogen pressure was raised to 80 pounds, the ultrasonic bath was switched on and valve 28 was opened to begin packing of the column. A timer was set for 10 minutes and packing allowed to continue for this period. The ultrasonic bath was switched off and valve 28 was then closed and the residual pressure allowed to bleed from the effluent line.

While specific embodiments of the chromatographic column packing method of the present invention have been disclosed in the foregoing description, it will be understood that various modifications within the spirit of the invention may occur to those skilled in the art. Therefore, it is intended that no limitations be placed on the invention except as defined by the scope of the appended claims.

We claim:

1. A method of packing a chromatographic column which comprises introducing a packing material into a chromatographic column in a predetermined direction under the influence of a first pressure differential and in the substantial absence of substantially regular periodic vibration until said chromatographic column is filled to a desired extent with said packing material, and subsequently establishing a substantially regular periodic vibration along the length of said column and subjecting said packing material to a second pressure differential therein, said first and second pressure differentials being applied in said predetermined direction so as to aid in filling and packing said column with said packing material.

2. The method of claim 1 wherein said second pressure differential is greater than said first pressure differential.

3. The method of claim 1 wherein said subsequently established substantially regular periodic vibration comprises ultrasonic vibration.

4. The method of claim 3 wherein said ultrasonic vibration is produced by immersing said column in a liquid-containing bath and subjecting said liquid in said bath to ultrasonic vibration.

5. The method of claim 4 wherein said ultrasonic vibration has a frequency greater than about 15 kilocycles per second.

6. The method of claim 1 wherein said first and second pressure differentials are produced at least in part by introducing a fluid stream into said column in said predetermined direction.

7. The method of claim 6 wherein said fluid comprises an inert gas.

8. The method of claim 7 wherein said inert gas is contacted with a source of radiation prior to its entry into said column.

9. The method of claim 6 including substantially abating said first pressure differential prior to establishing said substantially regular periodic vibration along the length of said column.

10. The method of claim 9 wherein said column is subjected to said second pressure differential immediately subsequent to the establishment of said substantially regular periodic vibration along the length of said column.

11. The method of claim 10 wherein said second pressure differential is established substantially instantaneously.

12. The method of claim 1 including applying an irregular vibration to said column during the introduction of said packing material under the influence of said first pressure differential.

13. The method of claim 12 wherein said irregular vibration is produced by tapping intermittently on said column.

14. The method of claim 6 including reducing the residual pressure in said column after the termination of said second pressure differential therein.

15. The method of claim 1 wherein said first and second pressure differentials are produced at least in part by applying a vacuum to one end of said column.

16. The method of claim 2 wherein said column has an inner diameter of between about 0.7 and 1.2 millimeters, said first pressure differential ranges between about 5 and 50 psid per yard of column length and said second pressure differential ranges between about 50 and 500 psid per yard of column length.

17. The method of claim 2 wherein said column has an inner diameter of greater than about 1.2 millimeters, said first pressure differential ranges between about 5 and 25 psid per yard of column length and said second pressure differential ranges between about 25 to 250 psid per yard of column length.

18. The method of claim 16 wherein said packing material has an average particle size of between about 5 and 200.

19. The method of claim 18 wherein said packing material is selected from a group consisting of diatomaceous earth, alumina, glass beads, Teflon beads, graphitized carbon black, molecular sieves, silica gel, and mixtures thereof.

20. The method of claim 1 wherein said packing material has an average particle size of between about 5 and 75 microns, and further wherein said chromatographic column has an inner diameter of between about 0.7 and 1.2 millimeters.

21. The method of claim 1 wherein said packing material has an average particle size of between about 50 and 200 microns and wherein said chromatographic column has an inner diameter of greater than about 1.2 millimeters.

22. The method of claim 1 wherein the introduction of said packing material into said column under the influence of said first pressure differential comprises a plurality of steps, with a portion of said packing material being introduced into said column in each of said steps.

23. The method of claim 22 including applying an irregular vibration to said column during each of said plurality of steps.

24. The method of claim 1 wherein said substantially regular periodic vibration is maintained for a period of from about 5 to 30 minutes while subjecting said packing material to said second pressure differential.

25. A method of packing a chromatographic column comprising:
(i) introducing a packing material, in the substantial absence of regular periodic vibration, into a chromatographic column under the influence of a first pressure differential ranging from about 5 to 50 psid per yard of column length until said column is filled with the packing material;
(ii) subjecting said filled column, while under the influence of said first pressure differential, to ultrasonic vibration;
(iii) increasing said pressure differential, while maintaining said ultrasonic vibration to a second pressure differential greater than said first pressure differential and ranging from about 50 to 500 psid per yard of column length for a period of from about 5 minutes to 10 hours; and thereafter
(iv) terminating the ultrasonic vibration and pressure differential.

26. A method of packing a chromatographic column as defined in claim 25 wherein the first and/or second pressure differentials are maintained by introducing an inert gas stream into said column.

27. The method of packing a chromatographic column as defined in claim 26 wherein said gas stream is passed into contact with a radiation source prior to entry into said column.

28. A method of packing a chromatographic column as defined in claim 25 wherein said ultrasonic vibration is imparted to the packing material in said column by immersing said column in a water bath and subjecting said water to ultrasonic vibrations having a frequency greater than about 15 kilohertz.

29. A method of packing a chromatographic column as defined in claim 25 wherein the passageway through the chromatographic column is coated with a non-reactive metal.

30. A method of packing a chromatographic column as defined in claim 29 wherein the non-reactive metal is gold.

31. A method of packing a chromatographic column which comprises introducing a packing material into a chromatographic column under the influence of a first pressure differential and in the substantial absence of substantially regular periodic vibration until said chromatographic column is filled to a desired extent with said packing material, and subsequently establishing a substantially regular periodic vibration along the length of said column and subjecting said packing material to a second pressure differential therein, said substantially regular periodic vibration comprising ultrasonic vibration.

32. The method of claim 31 wherein said ultrasonic vibration is produced by immersing said column in a liquid containing bath and subjecting said liquid in said bath to ultrasonic vibration.

33. The method of claim 32 wherein said ultrasonic vibration has a frequency greater than about 15 kilocycles per second.

* * * * *